United States Patent [19]

Butler et al.

[11] Patent Number: 4,548,947

[45] Date of Patent: Oct. 22, 1985

[54] 1-(SUBSTITUTED-ARYL)-DIHYDRO-1H-PYRROLIZINE-3,5-[2H,6H-]DIONES AND USE FOR REVERSING AMNESIA

[75] Inventors: Donald E. Butler; Anthony J. Thomas, both of Ann Arbor, Mich.

[73] Assignee: Warner-Lambert Company, Morris Plains, N.J.

[21] Appl. No.: 607,375

[22] Filed: May 7, 1984

[51] Int. Cl.[4] .................. A61K 31/40; C07P 487/06
[52] U.S. Cl. .................................. 514/413; 548/453

[58] Field of Search ................. 548/453; 424/274; 514/413

Primary Examiner—Richard L. Raymond
Assistant Examiner—D. B. Springer
Attorney, Agent, or Firm—Jerry F. Janssen

[57] ABSTRACT

1-(Substituted-aryl)-dihydro-1H-pyrrolizine-3,5-[2H,6H]-diones are effective cognition activating agents for the treatment of senility and for reversing amnesia. Pharmaceutical compositions containing these compounds and a method of treating senility or of reversing amnesia are also disclosed.

17 Claims, No Drawings

1-(SUBSTITUTED-ARYL)-DIHYDRO-1H-PYRROLIZINE-3,5-[2H,6H-]DIONES AND USE FOR REVERSING AMNESIA

BACKGROUND OF THE INVENTION

The present invention relates to compounds, pharmaceutical compositions, and a method of treating senility and reversing amnesia. More particularly, it is concerned with certain 1-(substituted-aryl)-dihydro-1$\underline{H}$-pyrrolizine 3,5-[2$\underline{H}$,6$\underline{H}$]-diones, pharmaceutical compositions containing these compounds, and a method of treating senility and reversing amnesia.

SUMMARY AND DETAILED DESCRIPTION

In its broadest aspect, the present invention relates to compounds having structural formula I:

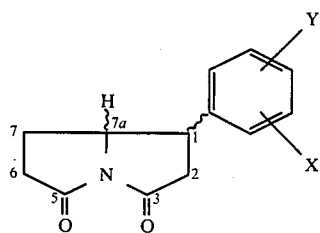

wherein X and Y are independently hydrogen, alkyl of from one to six carbon atoms, alkoxy of from one to six carbon atoms, chloro- or trifluoromethyl.

The ring-closure reactions (discussed further below) leading to compounds of the present invention produce compounds in which the aryl group may be in either a cis- or trans-configuration to the hydrogen atom at position 7a. The wavy lines in the structural formula presented above are meant to indicate all geometric isomeric possibilities.

In addition to this geometric isomerism, the introduction during the reaction sequence of two chiral centers at positions 1 and 7a in the structure asymmetric above permits the possible existence of four stereoisomeric forms (two diastereomeric pairs) of the compounds.

The present invention contemplates all possible stereoisomers and geometric isomers of the compounds represented by structural formula I, as well as mixtures thereof.

The terms "geometric isomers," "enantiomeric forms," and "stereoisomers" are those understood by practitioners of the organic chemical art, more specifically, as defined by E. L. Eliel, "Stereochemistry of Carbon Compounds," McGraw-Hill, New York, 1962.

By the term "alkyl of from one to six carbon atoms" is meant any branched or unbranched saturated hydrocarbon grouping containing from one to six carbon atoms. Such groups include, by way of example, methyl, ethyl, n-propyl, iso-propyl, n-, sec-, iso-, and tert-butyl, n-, sec-, iso-, and neo-pentyl, n-hexyl, and the like.

By the term "alkoxy of from one to six carbon atoms: is meant any moiety containing an alkyl group as defined above, attached through an oxygen atom to the parent molecular subunit.

The compounds of the present invention may also exist in the solvated form in which the compound is solvated with water, lower alcohols such as ethanol, propanol and the like, or other pharmaceutically acceptable solvents employed in the synthesis of the materials. Although the solvated and unsolvated forms of the compounds may differ somewhat in their physical properties such as melting point and solubility, they are considered equivalent for the purposes of the invention.

Representative examples of compounds contemplated as falling within the scope of the present invention cis-Dihydro-1-phenyl-1$\underline{H}$-pyrrolizine-3,5[2$\underline{H}$,6$\underline{H}$]-dione.

trans-Dihydro-1-phenyl-1$\underline{H}$-pyrrolizine-3,5[2$\underline{H}$,6$\underline{H}$]-dione.

cis-Dihydro-1-(methylphenyl)-1$\underline{H}$-pyrrolizine-3,5-[2$\underline{H}$,6$\underline{H}$]-dione.

trans-Dihydro-1-(methylphenyl)-1$\underline{H}$-pyrrolizine-3,5[2$\underline{H}$,6$\underline{H}$]-dione.

cis-Dihydro-1-(4-chlorophenyl)-1$\underline{H}$-pyrrolizine-3,5[2$\underline{H}$,6$\underline{H}$]-dione.

trans-Dihydro-1-(4-chlorophenyl)-1$\underline{H}$-pyrrolizine-3,5[2$\underline{H}$,6$\underline{H}$]-dione.

cis-Dihydro-1-(3,4-dichlorophenyl)-1$\underline{H}$-pyrrolizine-3,5[2$\underline{H}$,6$\underline{H}$]-dione.

trans-Dihydro-1-(3,4-dichlorophenyl)-1$\underline{H}$-pyrrolizine-3,5[2$\underline{H}$,6$\underline{H}$]-dione.

cis-Dihydro-1-(4-trifluoromethylphenyl)-1$\underline{H}$-pyrrolizine-3,5[2$\underline{H}$,6$\underline{H}$]-dione.

trans-Dihydro-1-(4-trifluoromethylphenyl)-1$\underline{H}$-pyrrolizine-3,5[2$\underline{H}$,6$\underline{H}$]-dione.

cis-Dihydro-1-(4-methoxyphenyl)-1$\underline{H}$-pyrrolizine-3,5[2$\underline{H}$,6$\underline{H}$]-dione.

trans-Dihydro-1-(4-methoxyphenyl)-1$\underline{H}$-pyrrolizine-3,5[2$\underline{H}$,6$\underline{H}$]-dione.

Compounds of the present invention, corresponding to structural formula I above, are prepared by cyclizing a compound having the general formula VI, wherein X and Y have the values defined above, and R and R' may be the same or different and are selected from methyl, ethyl, 1,1-dimethylethyl, phenyl, or phenylmethyl.

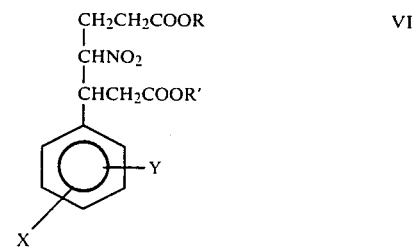

The following general reaction scheme illustrates methods of preparing compounds in accordance with this invention:

REACTION SCHEME

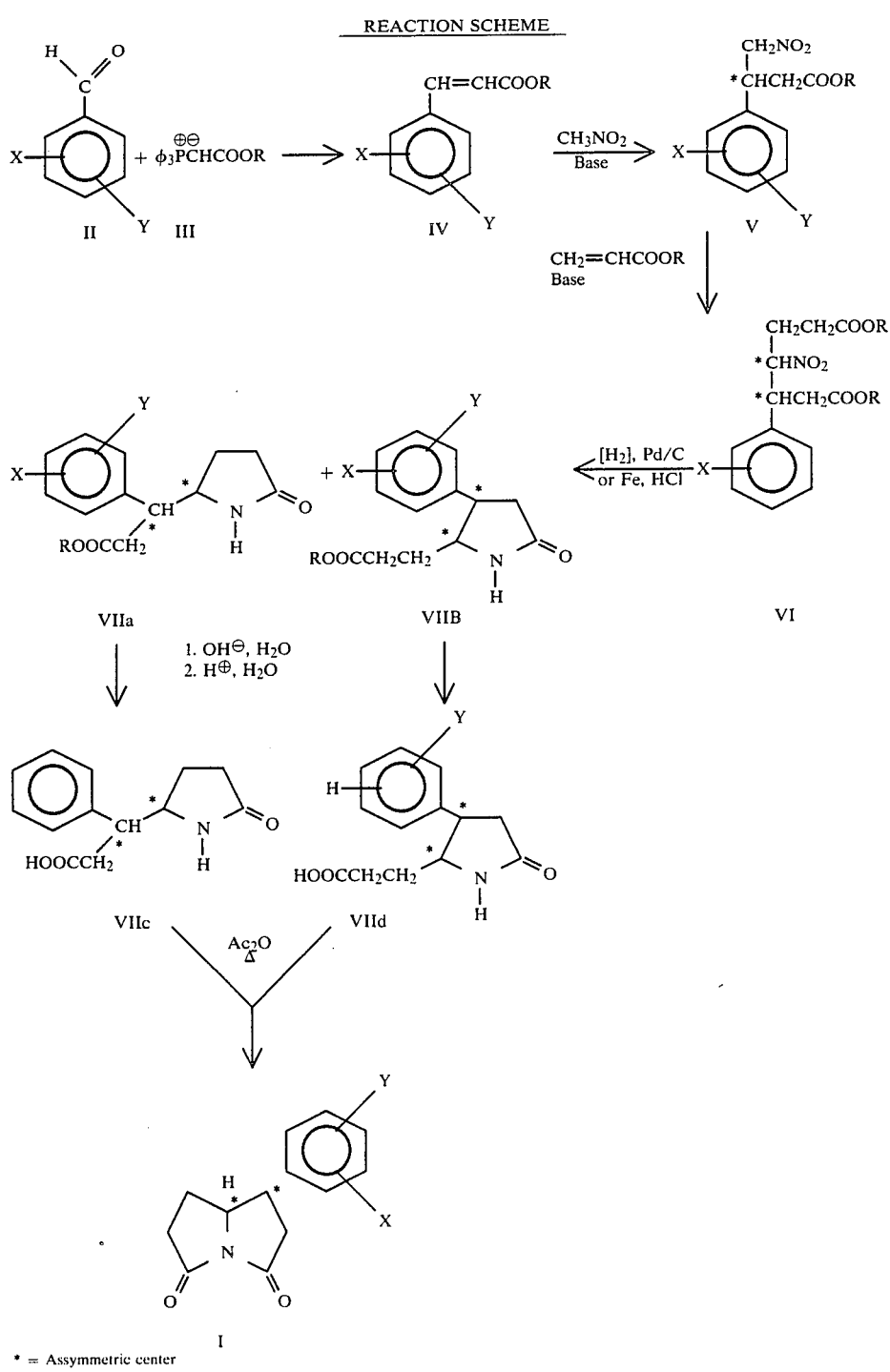

\* = Assymmetric center

The known mono-or disubstituted benzaldehydes, II, are reacted with the phosphorus ylid III (where R is methyl, ethyl, 1,1-dimethylethyl, phenyl, or phenylmethyl) to yield the substituted cinnamic acid esters IV in the well-known Wittig Reaction (cf. U. Schöllkopf, Ang. Chem., 71:260, 1959).

Reaction of IV with nitromethane in the presence of a basic catalyst produces the nitro-derivatives V. This reaction introduces an asymmetric center at the carbon atom attached to the aryl ring.

Condensation of the nitro-derivative, V, with an acrylic ester, VI (where R is as previously defined), in the presence of base introduces a second asymmetric center immediately adjacent to the first, and yields VI.

Reduction of VI, either by hydrogen over palladium/carbon catalyst, or by dissolving metal reduction employing, for example, iron and hydrochloric acid, yields the mixture of aryl-substituted pyrrolidonepropanoic acid esters, VIIa and VIIb. The esters VIIa and VIIb are hydrolyzed to their corresponding acids, VIIc and VIId, which are cyclized to the bicyclic compounds of formula I by the action of hot acetic anhydride.

Also in accordance with the present invention, pharmaceutical compositions may be produced by formulating compounds having structural formula I above in unit dosage form with a pharmaceutically acceptable carrier. Some examples of unit dosage forms are tablets, capsules, lozenges, and pills; as well as powders and aqueous and nonaqueous solutions and suspensions packaged in containers containing either one, or some larger number of dosage units and capable of being subdivided into individual doses by such means as measurement into a teaspoon or other standard container.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; galatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents, including other cognition activating agents such as 3-phenoxypyridine, and N-[N'N'-diisopropylaminoethyl]pyrrolidine-2-oxo-1-acetamide.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention contain from 0.1 to 250.0 mg, preferably from 1 to 25 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per day, preferably between about 25 mg to 750 mg per day, optionally administered in portions.

The compounds of the present invention are useful for treating senility or for reversing amnesia. The effectiveness of these compounds was evaluated by a test designed to show the ability of a given substance to reverse amnesia induced by electroconvulsive shock. The test is more fully described in U.S. Pat. No. 4,154,347, issued Mar. 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted employing compounds of the present invention appear in the Table I. The following criteria were used in interpreting the data: 40% or more amnesia reversal in the test animals=active, A; 25% to 39% amnesia reversal=borderline activity, C; 0% to 24% reversal of amnesia=inactive, N.

TABLE

| Compound | X | Y | Stereo-Chemistry* | Activity 100 mg/kg | 10 mg/kg | 1 mg/kg |
|---|---|---|---|---|---|---|
| 1 | H | H | c-t | 42(A) | 25(C) | 50(A) |
| 2 | H | H | c | 0 | 0(N) | 50(A) |
| 3 | H | H | t | 42(A) | 68(A) | 25(C) |
| 4 | 4-CH₃ | H | c-t | 83(A) | 6(N) | 58(A) |
| 5 | 4-CF₃ | H | c-t | 24(N) | 56(A) | 54(A) |
| 6 | Cl | Cl | c-t | | | |
| 7 | 4-Cl | H | c-t | | | |
| 8 | 4-CH₃O | H | c-t | | | |

*c = Cis-configuration of 1-aryl-substitutent relative to 7a hydrogen atom.
t = Trans-configuration of 1-aryl-substitutent relative to 7a hydrogen atom.

The following examples are provided to enable one skilled in the art to practice the invention. These examples are not to be read as limiting the scope of the present invention as defined by the appended claims, but as merely illustrated thereof.

EXAMPLE 1

Preparation of 4-nitro-3-phenylheptanedioic acid dimethyl ester.

A mixture of 300 g of cinnamic acid methyl ester, 500 g of nitromethane and 39 g of tetramethylguanidine is allowed to stir at room temperature for 72 hours. The solution is diluted with diethyl ether and aqueous hydrochloric acid solution (1 N, 1 liter) is added. The organic layer is separated dried over anhydrous magnesium sulfate, and evaporated to give 4-nitro-3-phenylbutanoic acid methyl ester.

NMR (CDCl₃) δ=7.25 (s, 5H); 4.70 (d, J=14 Hz, 2H), 3.98 (m, J=14 Hz, 1H); 3.59 (s, 3H); 2.77 (d, J=14 Hz, 2H).

IR (cm⁻¹) 3030, 2960, 1735, 1600, 1550.

A solution of 356 g of nitro-3-phenylbutanoic acid methyl ester, 138 g of methyl acrylate, and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-phenylheptanedioic acid dimethyl ester.

NMR (CDCl₃) δ=7.20 (m, 5H); 4.85 (m, 1H); 3.60 (s, 3H); 3.00–1.60 (m, 7H).

IR (cm$^{-1}$) 2960, 1740, 1552, 1440, 1367.

Preparation of, 5-oxo-3-phenyl-2-pyrrolidinepropanoic acid, 5-oxo-3-phenyl-2-pyrrolidinepropanoic acid methyl ester, 5-oxo-β-phenyl-2-pyrrolidinepropanoic acid, 5-oxo-β-phenyl-2-pyrrolidinepropanoic acid methyl ester A suspension of 120 g of 4-nitro-3-(phenyl)heptanedioic acid dimethyl ester and 5.5 g of 20% Pd/C in 1200 ml of methanol is placed under hydrogen atmosphere. After H$_2$ absorption is completed, the solution is filtered and the solvent is removed under reduced pressure to give a yellow oil that consists of a mixture of 5-oxo-3-phenyl-2-pyrrolidinepropanoic acid methyl ester, 5-oxo-β-phenyl-2-pyrrolidinepropanoic acid methyl ester and small amounts of the corresponding acids.

NMR (CDCl$_3$) δ=7.17 (s, 5H); 6.80 (s, 1H), 3.62 (m, 1H); 5.80 (s,3H); 3.20-1.72 (m, 7H).

IR (cm$^{-1}$) 3340, 3220, 3030, 2957, 1734, 1692, 1495, 1454, 1437.

A solution of 93.4 g of 5-oxo-3-phenyl-2-pyrrolidinepropanoic acid methyl ester and 5-oxo-β-phenyl-2-pyrrolidinepropanoic acid methyl ester in 370 ml of 1 N aqueous sodium hydroxide solution is heated to 60° C. for four hours. Excess aqueous hydrochloric acid (1 N, 380 ml) is added and the solution concentrated under reduced pressure to give 5-oxo-β-phenyl-2-pyrrolidinepropanoic acid and 5-oxo-3-phenyl-2-pyrrolidinepropanoic acid.

Preparation of trans-dihydro-1-phenyl-1H-pyrrolizine-3,5(2H,6H)-dione and cis-dihydro-1-phenyl-1H-pyrrolizine-3,5-(2H,6H)-dione (as a mixture)

A solution of 93.4 g of 5-oxo-3-phenyl-2-pyrrolidinepropanoic acid methyl ester and 5-oxo-β-phenyl-2-pyrrolidinepropanoic acid methyl ester in 370 ml of 1N aqueous sodium hydroxide solution is heated to 60° C. for four hours. Excess aqueous hydrochloric acid (1 N, 370 ml) is added and the solution is concentrated under reduced pressure to yield 5-oxo-β-phenyl-2-pyrrolidinepropanoic acid and 5-oxo-3-phenyl-2-pyrrolidinepropanoic acid. The acids are dissolved in 300 ml of acetic anhydride and the solution heated to 90° C. The solution is filtered hot and the filtrate concentrated in vacuo. The oil is chromatographed on silica gel (200-400 mesh) to give cis- and trans-dihydro-1-phenyl-1H-pyrrolizine-3,5(2H,6H)-diones as a white solid with mp 151°-3° C.

NMR (CDCl$_3$) δ=7.39 (m, 5H); 4.71 (dt, J$_1$=7 Hz, J$_2$=10 Hz, 1H); 4.46 (dt, J$_1$=10 Hz, J$_2$=6 Hz, 1H); 3.84-1.15 (m, 7H).

IR (cm$^{-1}$) 3025, 2990, 1775, 1695, 1603, 1500.

EXAMPLE 2

Separation of trans-dihydro-1-phenyl-1H-pyrrolizine-3,5(2H,6H)-dione and cis-dihydro-1-phenyl-1H-pyrrolizine-3,5(2H,6H)-dione Chromatography on SiO$_2$ (using a chromatotron elution with chloroform) gave trans-and cis-isomer separation with the following physical characteristics:

Characteristics of trans-dihydro-1-phenyl-1H-pyrrolizine-3,5[2H,6H]-dione.

NMR (CDCl$_3$) δ=7.39 (m, 5H); 4.40 (dt, J$_1$=10 Hz, J$_2$=6 Hz, 1H); 3.53-1.73 (m, 7H).

IR (cm$^{-1}$) 3030, 2980, 2900, 1769, 1695, 1605, 1496 mp 151°-3° C.

Characteristics of cis-dihydro-1-phenyl-1H-pyrrolizine-3,5(2H,6H-dione.

NMR (CDCl$_3$) δ=7.40 (m, 3H); 7.17 (m, 2H); 4.71 (dt, J$_1$=6 Hz, J$_2$=10 Hz, 1H); 3.70 (t, J$_1$=4 Hz, 1H); 3.27 (dd, J$_1$=4 Hz, J$_2$=4 Hz, 1H); 3.10-1.14 (m, 5H).

IR (cm$^{-1}$) 2995, 2900, 1778, 1695, 1603, 1500 mp 139°-42° C.

EXAMPLE 3

Preparation of 4-nitro-3-(4-methylphenyl)heptanedioic acid dimethyl ester

A suspension of 300 g of p-methylcinnamic acid (J. Chem. Soc., Chem. Comm., 471, 1976) and 25 ml of concentrated sulfuric acid in 1.7 liters of methanol is heated to reflux for 24 hours. The solution is concentrated, cooled and filtered to give as a white solid, p-methylcinnamic acid methyl ester, mp 55°-56° C.

NMR (DMSOd$_6$) δ=7.36 (d, J=16 Hz, 1H); 7.36 (dd, J$_1$=30 Hz, J$_2$=7 Hz, 4H); 6.48 (d, J=16 Hz, 1H); 3.70 (s, 3H); 2.32 (s, 3H). IR (cm$^{-1}$) 3061, 3028, 2949, 1713, 1634, 1607, 1570, 1516, 1438.

A mixture to 300 g of p-methylcinnamic acid, methyl ester, 500 g of nitromethane and 39 g of tetramethylguanidine is allowed to stir at room temperature for 72 hours. The solution is diluted with diethyl ether and (1 liter, 1 N) aqueous hydrochloric acid solution added. The organic layer is separated, dried over anhydrous magnesium sulfate, and evaporated to give 4-nitro-3-(4-methylphenyl) butanoic acid methyl ester.

NMR (CDCl$_3$) δ=7.10 (s, 4H); 4.63 (d, J=8 Hz, 2H); 3.91 (m, 1H); 3.56 (s, 3H); 2.78 (d, J=8 Hz, 2H); 2.25 (s, 3H).

IR (cm$^{-1}$) 2940, 1740, 1555, 1515, 1440, 1380, 1250, 1170.

A solution of 356 g of 4-nitro-3-(4-methylphenyl)-butanoic acid methyl ester, 138 g of methyl acrylate and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(4-methylphenyl)heptanedioic acid dimethyl ester.

NMR (CDCl$_3$) δ=7.13 (m, 4H); 4.83 (m, 1H); 3.66 (s, 3H); 3.60 (s, 3H); 3.10-1.77 (m, 10H).

IR (cm$^{-1}$) 2950, 1738, 1555, 1518, 1440, 1365, 1325, 1260.

Preparation of 3-(4-methylphenyl)-5-oxo-2-pyrrolidinepropanoic acid, 3-(4-methylphenyl)-5-oxo-2-pyrrolidinepropanoic acid methyl ester, β-(4-methylphenyl)-5-oxo-2-pyrrolidinepropanoic acid, β-(4-methylphenyl)-5-oxo-2-pyrrolidinepropanoic acid methyl ester A suspension of 120 g of 4-nitro-3-(4-methylphenyl)-heptanedioic acid dimethyl ester and 5.5 g of 20% Pd/C in 1200 ml of methanol is placed under hydrogen atmosphere. After H$_2$ absorption is completed, the solution is filtered and the solvent is removed under reduced pressure to give a yellow oil that consists of a mixture of 3-(4-methylphenyl)-5-oxo-2-pyrrolidinepropanoic acid methyl ester, β-(4-methylphenyl)-5-oxo-2-pyrrolidinepropanoic acid methyl ester, and small amounts of the corresponding acids.

NMR (CDCl₃) δ=7.50 (s, 4H); 7.21 (s, 1H); 4.02 (m, 1H); 3.32–1.75 (m, 10H). IR (cm⁻¹) 3190, 3000, 2925, 1730, 1685, 1540, 1490, 1450, 1435, 1360.

A solution of 93.4 g of 3-(4-methylphenyl)-5-oxo-2-pyrrolidinepropanoic acid methyl ester and β-(4methylphenyl)-5-oxo-2-pyrrolidinepropanoic acid methyl ester in 370 ml of 1 N aqueous sodium hydroxide solution is heated to 60° C. for four hours. Excess aqueous hydrochloric acid (1 N, 380 ml) is added and the solution is concentrated under reduced pressure to give β-(4-methylphenyl)-5-oxo-2-pyrrolidinepropanoic acid and 3-(4-methylphenyl)-5-oxo-2-pyrrolidinepropanoic acid.

Preparation of cis-and trans-dihydro-1-(4-methylphenyl)-1H-pyrrolizine-3,5(2H,6H)-diones A solution of 93.4 g of 3-(4-methylphenyl)-5-oxo-2-pyrrolidinepropanoic acid methyl ester and β-(4-methylphenyl)-5-oxo-2-pyrrolidinepropanoic acid methyl ester in 370 ml of 1 N aqueous sodium hydroxide solution is heated to 60° C. for four hours. Excess aqueous hydrochloric acid (1 N, 370 ml) is added and the solution concentrated under reduced pressure to give β-(4-methylphenyl)-5-oxo-2-pyrrolidinepropanoic acid and 3-(4-methylphenyl)-5-oxo-2-pyrrolidinepropanoic acid. The acids are dissolved in 300 ml of acetic anhydride, and the solution is heated to 90° C. The solution is filtered hot and the filtrate concentrated in vacuo. The oil is chromatographed on silica gel (200–400 mesh) (elution with chloroform) to give cis- and trans-dihydro-1-(4-methylphenyl)-1H-pyrrolizine-3,5(2H,6H)-diones as a white solid with mp 147°–150° C.

NMR (CDCl₃) δ=7.17 (m, 4H); 4.33 (dt, J₁=9 Hz, J₂=6 Hz, 1H); 3.55–1.60 (m, 10H). IR (cm⁻¹) 2985, 1789, 1700, 1494, 1454, 1383, 1362, 1320.

EXAMPLE 4

Preparation of 4-nitro-3-(4-chlorophenyl)hepanedioic acid dimethyl ester

A suspension of 300 g of 4-chlorocinnamic acid (J. Am. Chem. Soc., 89:3803, 1967) and 25 ml of concentrated sulfuric acid in 1.7 liters of methanol is heated to reflux for 24 hours. The solution is concentrated, and filtered to give as a white solid, p-chlorocinnamic acid methyl ester, mp 74°–5° C.

NMR (CDCl₃) δ=7.65 (d, J=16 Hz, 1H); 7.37 (m, 4H); 6.40 (d, J=16 Hz, 1H); 3.81 (s, 3H).

IR (cm⁻¹) 3036, 2952, 1710, 1670, 1635, 1593.

A mixture of 290 g of p-chlorocinnamic acid, methyl ester, 500 g of nitromethane and 39 g of tetramethylguanidine is allowed to stir for 72 hours. The solution is diluted with ethyl ether and aqueous hydrochloric acid solution (1 N, 1 liter) is added. The organic layer is separated, dried over anhydrous magnesium sulfate, and evaporated to give 4-nitro-3-(4-chlorophenyl)butanoic acid methyl ester.

NMR (CDCl₃) δ=7.23 (m, 4H); 4.73 (d, J=8 Hz, 2H); 4.10 (m, 1H); 3.65 (s, 3H); 2.75 (d, J=8 Hz, 2H).

IR (cm⁻¹) 2930, 1735, 1590, 1550, 1490, 1435, 1375, 1320.

A solution of 337 g of 4-nitro-3-(4-chlorophenyl)-butanoic acid methyl ester, 118 g of methyl acrylate, and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(4-chlorophenyl)heptanedioic acid dimethyl ester.

NMR (CDCl₃) δ=7.23 (m, 4H); 4.73 (m, 1H); 3.60 (s, 3H); 3.47 (s, 3H); 2.93–1.64 (m, 7H).

IR (cm⁻¹) 2940, 1740, 1555, 1470, 1440, 1365, 1250.

Preparation of 3-(4-chlorophenyl)-5-oxo-2-pyrrolidinepropanoic acid, 3-(4-chlorophenyl)-5-oxo-2-pyrrolidinepropanoic acid methyl ester, b-(4-chlorophenyl)-5-oxo-2-pyrrolidinepropanoic acid, β-(4-chlorophenyl)-5-oxo-2-pyrrolidinepropanoic acid methyl ester A suspension of 51.5 g 4-nitro-3-(4-chlorophenyl)heptanedioic acid dimethyl ester, 52 g of iron powder and 7 ml of concentrated hydrochloric acid in 500 ml ethanol/water (1:1) is heated to reflux for 14 hours. After filtering off the insolubles and evaporation of solvent, the resulting oil is chromatographed over silica gel (mesh size 200–400) (elution with chloroform) to give a mixture consisting of 3-(4-chlorophenyl)-5-oxo-2-pyrrolidinepropanoic acid methyl ester and β-(4-chlorophenyl)-5-oxo-2-pyrrolidinepropanoic acid methyl ester.

NMR (CDCl₃) δ=8.05 (s, 1H); 7.34 (m, 4H); 4.08 (m, 1H); 3.52 (s, 3H); 3.32–1.00 (m, 7H).

IR (cm⁻¹) 3200, 3050, 2930, 1725, 1680, 1585, 1430.

A solution of 36.7 g of 3-(4-chlorophenyl)-5-oxo-2-pyrrolidinepropanoic acid methyl ester and β-(4-chlorophenyl)-5-oxo-2-pyrrolidinepropanoic acid methyl ester in aqueous sodium hydroxide (1 N, 130 ml) solution is heated to 60° C. for four hours. Excess aqueous hydrochloric acid (1 N, 140 ml) is added and solution is concentrated under reduced pressure to give β-(4-chlorophenyl)-5-oxo-2-pyrrolidinepropanoic acid and 3-(4-chlorophenyl)-5-oxo-2-pyrrolidinepropanoic acid.

Preparation of cis-and trans-dihydro-1-(4-chlorophenyl)-1H-pyrrolizine-3,5(2H,6H)-diones A solution of 36.7 g of 3-(4-chlorophenyl)-5-oxo-2-pyrrolidinepropanoic acid methyl ester and β-(4-chlorophenyl)-5-oxo-2-pyrrolidinepropanoic acid methyl ester in 130 ml of 1 N aqueous sodium hydroxide solution is heated to 60° C. for four hours. Excess aqueous hydrochloric acid (1 N, 140 ml) is added and the solution concentrated under reduced pressure to give β-(4-chlorophenyl)-5-oxo-2-pyrrolidinepropanoic acid and 3-(4-chlorophenyl)-5-oxo-2-pyrrolidinepropanoic acid. The acids are dissolved in 100 ml of acetic anhydride and the solution heated to 90° C. The solution is filtered hot and the filtrate concentrated in vacuo. The oil is chromatographed on silica gel (200–400 mesh) (elution with chloroform) to yield cis-and trans-dihydro-1-(4-chlorophenyl)-1H-pyrrolizine-3,5(2H,6H)diones as a white solid with mp 153°–58° C.

NMR (CDCl₃) δ=7.17 (m, 4H); 4.33 (dt, J₁=9 Hz, J₂=6 Hz, 1H); 3.55–1.60 (m, 7H).

IR (cm⁻¹) 2985, 1789, 1700, 1494, 1383, 1362, 1320.

EXAMPLE 5

Preparation of 4-nitro-3-(3,4-dichlorophenyl)heptanedioic acid dimethyl ester

A suspension of 300 g of 3,4-dichlorocinnamic acid (J. Org. Chem., 26:2991 (1961)) and 25 ml of concentrated sulfuric acid in 1.7 liters of methanol is heated to reflux for 24 hours. The solution is concentrated, cooled, and filtered to give as a white solid, 3,4-dichlorocinnamic acid methyl ester, mp 114°–15° C.

NMR (CDCl$_3$) δ=7.40 (m, 4H); 6.33 (d, J=16 Hz, 1H); 3.72 (s, 3H).

IR (cm$^{-1}$) 3093, 3035, 1719, 1643, 1483, 1434, 1322, 1213.

A mixture of 300 g of 3,4-dichlorocinnamic acid methyl ester, 400 g of nitromethane and 26 g of tetramethylguanidine is allowed to stir for 72 hours. The solution is diluted with ethyl ether and aqueous hydrochloric acid solution (1 N, 1 liter) is added. The organic layer is separated, dried over anhydrous magnesium sulfate, and evaporated to give 4-nitro-3-(3,4-dichlorophenyl)butanoic acid methyl ester.

NMR (CDCl$_3$) δ=7.27 (m, 3H); 4.70 (d, J=8 Hz, 2H); 4.00 (m, 1H); 3.62 (s, 3H); 2.76 (d, J=8 Hz, 2H).

IR (cm$^{-1}$) 2950, 2880, 1725, 1549, 1410, 1265, 1090, 1015, 800.

A solution of 350 g of nitro-3-(3,4-dichlorophenyl)-butanoic acid methyl ester, 118 g of methyl acrylate and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(3,4-dichlorophenyl)heptanedioic acid dimethyl ester.

NMR (CDCl$_3$) δ=7.20 (m, 3H); 4.84 (m, 1H); 4.10 (m, 1H); 3.60 (s, 3H); 3.50 (s, 3H); 3.17–1.67 (m, 6H).

IR (cm$^{-1}$) 2970, 1725, 1555, 1495, 1440, 1420, 1375.

Preparation of
3-(3,4-dichlorophenyl)-5-oxo-2-pyrrolidinepropanoic acid,
3-(3,4-dichlorophenyl)-5-oxo-2-pyrrolidinepropanoic acid methyl ester,
β-(3,4-dichlorophenyl)-5-oxo-2-pyrrolidinepropanoic acid,
β-(3,4-dichlorophenyl)-5-oxo-2-pyrrolidinepropanoic acid methyl ester A suspension of 56.6 g 4-nitro-(3,4-dichlorophenyl) heptanedioic acid dimethyl ester, 60 g of iron powder and 7 ml of concentrated hydrochloric acid in 500 ml ethanol/water (1:1) is heated to reflux for 14 hours. After filtering off the insolubles and evaporation of the solvent, the resulting oil is chromagraphed over silica gel (mesh size 200–400) (elution with chloroform) to give a mixture that consists of 3-(3,4-dichlorophenyl)-5-oxo-2-pyrrolidinepropanoic acid methyl ester and β-(3,4-dichlorophenyl)-5-oxo-2-pyrrolidinepropanoic acid methyl ester.

NNR (CDCl$_3$) δ=7.51 (s, 1H); 7.11 (m, 3H); 4.14 (m, 1H); 3.62 (s, 3H); 3.05–1.72 (m, 7H).

IR (cm$^{-1}$) 3175, 3070, 2925, 1725, 1690, 1580, 1540, 1465, 1430.

A solution of 34.1 g of 3-(3,4-dichlorophenyl)-5-oxo-2-pyrrolidinepropanoic acid methyl ester and β-(3,4-dichlorophenyl)-5-oxo-2-pyrrolidinepropanoic acid methyl ester in aqueous sodium hydroxide solution (1 N, 108 ml) is heated to 60° C. for four hours. Excess aqueous hydrochloric acid (1 N, 120 ml) is added and the solution is concentrated under reduced pressure to give β-(3,4-dichlorophenyl)-5-oxo-2-pyrrolidine-propanoic acid and 3-(3,4-dichlorophenyl)-5-oxo-2-pyrrolidinepropanoic acid.

Preparation of cis-and trans-dihydro-1-(3,4-dichlorophenyl)-1H-pyrrolizine-3,5(2H,6H)-diones A solution of 34.1 g of 3-(3,4-dichlorophenyl)-5-oxo-2-pyrrolidinepropanoic acid methyl ester and β-(3,4-dichlorophenyl)-5-oxo-2-pyrrolidinepropanoic acid methyl ester in 110 ml of 1 N aqueous sodium hydroxide solution is heated to 60° C. for four hours. Excess aqueous hydrochloric acid (1 N, 120 ml) is added and the solution concentrated under reduced pressure to give β-(3,4-dichlorophenyl)-5-oxo-2-pyrrolidinepropanoic acid, and 3-(3,4-dichlorophenyl)-5-oxo-2-pyrrolidinepropanoic acid. The acids are dissolved in 100 ml of acetic anhydride, and the solution is heated to 90° C. The solution is filtered hot and the filtrate concentrated in vacuo. The oil is chromatographed on silica gel (200–400 mesh) (elution with chloroform) to give cis- and transdihydro-1-(3,4-dichlorophenyl)-1H-pyrrolizine-3,5(2H, 6H)-diones as a white solid with mp 161°–167° C.

NMR (CDCL$_3$) δ=7.01 (m, 3H); 4.29 (dt, J$_1$=10 Hz, J$_2$=6 Hz, 1H); 3.48–1.50 (m, 7H).

IR (cm$^{-1}$) 2985, 2920, 1781, 1696, 1597, 1562, 1478, 1420, 1406.

EXAMPLE 6

Preparation of
4-nitro-3-(4-trifluoromethylphenyl)heptanedioic acid ethyl, methyl ester A suspension of 300 g of 4-trifluoromethylcinnamic acid (*J. Org. Chem.* 43:980 (1980) and 25 ml of concentrated sulfuric acid in 1.7 liters of ethanol is heated to reflux for 24 hours. The solution is concentrated, cooled, and filtered to give as a white solid, 4-trifluoromethylcinnamic acid ethyl ester, mp 40°–41° C.

NMR (CDCl$_3$) δ=7.83 (m, 4H); 7.68 (d, J=15 Hz, 1H); 6.75 (d, J=15 Hz, 1H); 4.19 (q, J=6 Hz, 2H); 1.20 (t, J=6 Hz, 3H).

IR (cm$^{-1}$) 2980, 1715, 1644, 1479, 1442, 1368, 1336.

A mixture of 300 g of 4-trifluoromethylcinnamic acid ethyl ester, 500 g of nitromethane, and 39 g of tetramethylguanidine is allowed to stir for 72 hours. The solution is diluted with diethyl ether and aqueous hydrochloric acid solution (1 N, 1 liter) is added. The organic layer is separated, dried over anhydrous magnesium sulfate and evaporated to give 4-nitro-3-(4-trifluoromethylphenyl)butanoic acid ethyl ester.

NMR (CDCl$_3$) δ=7.54 (s, 4H); 4.76 (d, J=18 Hz, 2H); 4.15 (m, 1H); 4.10 (q, J=17 Hz, 2H); 2.80 (d, J=8 Hz, 2H); 1.17 (t, J=7 Hz, 3H).

IR (CM$^{-1}$) 2970, 1735, 1555, 1455, 1380, 1330.

A solution of 356 g of 4-nitro-3-(4-trifluoromethylphenyl)butanoic acid ethyl ester, 138 g of methyl acrylate, and 25 ml of Triton B in 500 ml of butanol is allowed to stir at room temperature for 94 hours. Excess aqueous hydrochloric acid (1 N), is added and the solution is diluted with diethyl ether. The organic layer is separated, dried over anhydrous nagnesium sulfate and evaporated to give 4-nitro-3-(4-trifluoromethylphenyl)-heptanedioic acid ethyl, methyl ester.

NMR (CDCl$_3$) δ=7.44 (s, 4H); 4.82 (m, 1H); 3.65 (s, 3H); 3.58 (s, 3H); 3.22–1.70 (m, 7H).

IR (cm$^{-1}$) 2910, 2840, 1740, 1540, 1460, 1375.

Preparation of 5-oxo-3-[4-(trifluoromethyl)phenyl]-2-pyrrolidinepropanoic acid, 5-oxo-3-[4-(trifluoromethyl)phenyl]-2-pyrrolidinepropanoic acid methyl ester, 5-oxo-β-[4-(trifluoromethyl)phenyl]-2-pyrrolidinepropanoic acid, 5-oxo-β-[4-(trifluoromethyl)phenyl]-2-pyrrolidinepropanoic acid ethyl ester.

A suspension of 120 g of 4-nitro-3-(4-trifluoromethyl)heptanedioic acid ethyl, methyl ester and 5.5 g of 20% Pd/C in 1200 ml of methanol is placed under hydrogen atmosphere. After $H_2$ absorption is complete, the solution is filtered and the methanol removed under reduced pressure to give a yellow oil that consists of a mixture of 5-oxo-3-[4-(trifluoromethyl)phenyl]-2-pyrrolidinepropanoic acid methyl ester and 5-oxo-β-[4-(trifluoromethyl)phenyl]-2-pyrrolidinepropanoic acid ethyl ester, and small amounts of the corresponding acids. NMR (CDCl$_3$) δ=8.35 (s, 1H); 7.53 (s, 4H); 4.15 (m, 3H); 3.60–1.75 (m, 7H); 1.20 (m, 3H). IR (cm$^{-1}$) 3200, 3010, 1725, 1690, 1540, 1450, 1380, 1330.

A solution of 93.4 g of 5-oxo-3-[4-(trifluoromethyl)phenyl]-2-pyrrolidinepropanoic acid methyl ester and 5-oxo-β-[4-trifluoromethyl)phenyl]-2-pyrrolidinepropanoic acid ethyl ester in aqueous sodium hydroxide solution (1 N, 370 ml) is heated to 60° C. for four hours. Excess aqueous hydrochloric acid (1 N, 370 ml) is added and the solution is con25 centrated under reduced pressure to give 5-oxo-β-[4-(trifluoromethyl)phenyl]-2-pyrrolidinepropanoic acid and 5-oxo-3-[4-(trifluoromethyl)phenyl]-2-pyrrolidinepropanoic acid.

Preparation of cis-and trans-dihydro-1-(4-trifluoromethylphenyl)-1H-pyrrolizine-3,5(2H,6H)-diones A solution of 93.4 g of 5-oxo-3-[4-(trifluoromethyl)phenyl]-2-pyrrolidinepropanoic acid methyl ester and 5-oxo-β-[4-(trifluoromethyl)phenyl]-2-pyrrolidinepropanoic acid methyl ester in 370 ml of 1 N aqueous sodium hydroxide solution is heated to 60° C. for four hours. Excess aqueous hydrochloric acid (1 N, 380 ml) is added and the solution concentrated under reduced pressure to give 5-oxo-β-[4-(trifluoromethyl)phenyl]-2-pyrrolidinepropanoic acid and 5-oxo-3-[4-(trifluoromethyl)phenyl]-2-pyrrolidinepropanoic acid. The acids are dissolved in 300 ml of acetic anhydride, and the solution is heated to 90° C. The solution is filtered hot and the filtrate concentrated in vacuo. The oil is chromatographed on silica gel (200–400 mesh) (elution with chloroform) to give cis-and trans-dihydro-1-(4-trifluoromethylphenyl)-1H-pyrrolizine-3,5-(2H,6H)-diones as a white solid with a mp 173°–181° C.

NMR (CDCl$_3$) δ=7.32 (s, 4H); 4.36 (dt, J$_1$=9 Hz, J$_2$=5 Hz, 1H); 3.60–1.71 (m, 7H).

IR (cm$^{-1}$) 2988, 1786, 1697, 1595, 1493, 1459, 1444, 1425.

EXAMPLE 7

Preparation of 4-nitro-3-(4-methoxyphenyl)heptanedioic acid dimethyl ester

A suspension of 300 g of 4-methoxycinnamic acid (*J. Chem. Soc., Chem. Comm.*, 355, (1978)) and 25 ml of concentrated sulfuric acid in 1.7 liters of methanol is heated to reflux for 96 hours. The solution is concentrated, cooled, and filtered to give as a white solid, 4-methoxycinnamic acid methyl ester, mp 85°–86° C.

NMR (DMSOd$_6$) δ=7.53 (d, J=15 Hz, 1H); 7.48 (d, J=9 Hz, 2H); 6.88 (d, J=9 Hz, 2H), 6.38 (d, J=15 Hz, 1H); 3.75 (s, 3H); 3.67 (s, 3H).

IR (cm$^{-1}$) 2951, 2845, 1715, 1638, 1605, 1577, 1514.

A mixture of 288 g of 4-methoxycinnamic acid methyl ester, 500 g of nitromethane and 23 g of tetramethylguanidine is allowed to stir for 72 hours. The solution is diluted with diethyl ether and aqueous hydrochloric acid solution (1 N, 1 liter) is added. The organic layer is separated, dried over anhydrous magnesium sulfate, and evaporated to give 4-nitro-3-(4-methoxyphenyl)butanoic acid methyl ester.

NMR (CDCl$_3$) δ=6.89 (m, 4H), 4.00 (d, J=14 Hz, 2H); 3.84 (m, 1H); 3.63 (s, 3H); 3.42 (s, 3H); 2.60 (d, J=14 Hz, 2H).

IR (cm$^{-1}$) 3004, 2954, 2840, 1737, 1635, 1605, 1585, 1577, 1554.

A solution of 200 g of 4-nitro-3-(4-methoxyphenyl)-butanoic acid methyl ester, 68 g of methyl acrylate, and 25 ml of Triton B in 500 ml of t-butanol is allowed to stir at room temperature for 94 hours. Excess aqeous hydrochloric acid (1 N) is added and the solution is diluted with diethyl ether. The organic layer is separated, dried over anhydrous magnesium sulfate, and evaporated to give 4-nitro-3-(4-methoxyphenyl)heptanedioic acid dimethyl ester.

NMR (CDCl$_3$) δ=6.90 (m, 4H); 3.78–3.27 (m, 10H); 2.90–1.77 (m, 7H).

IR (cm$^{-1}$) 2975, 2930, 2810, 1730, 1630, 1600, 1550, 1510, 1480, 1440, 1380.

Preparation of 3-(4-methyoxyphenyl)-5-oxo-2-pyrrolidinepropanoic acid, 3-(4-methyoxyphenyl)-5-oxo-2-pyrrolidinepropanoic acid methyl ester, β-(4-methoxyphenyl)-5-oxo-2-pyrrolidinepropanoic acid, β-(4-methoxyphenyl)-5-oxo-2-pyrrolidinepropanoic acid methyl ester A suspension of 120 g of 4-nitro-3-(4-methoxyphenyl)heptanedioic acid dimethyl ester and 5.5 g of 20% Pd/C in 120 ml of methanol is placed under hydrogen atmosphere. After $H_2$ absorption is complete, the solution is filtered and the solvent removed under reduced pressure to give a yellow oil that consists of a mixture of 3-(4-methoxyphenyl)-5-oxo-2-pyrrolidinepropanoic acid methyl ester and β-(4-methoxyphenyl)-5-oxo-2-pyrrolidinepropanoic acid methyl ester and small amounts of the corresponding acids.

NMR (CDCl$_3$) δ=7.87 (s, 1H); 6.90 (m, 4H); 3.77 (s, 3H); 3.67 (s, 3H); 3.50 (m, 1H); 3.10–1.60 (m, 7H).

IR (cm$^{-1}$) 3630, 3560, 2990, 1725, 1690, 1600, 1505, 1430.

Preparation of cis- and trans-dihydro-1-(4-methoxyphenyl)-1H-pyrrolizine-3,5(2H,6H)-diones A solution of 132.3 g of 3-(4-methoxyphenyl)-5-oxo-2-pyrrolidinepropanoic acid methyl ester and β-(4-methoxyphenyl)-5-oxo-2-pyrrolidinepropanoic acid methyl ester in 480 ml of 1 N aqueous sodium hydroxide solution is heated to 60° C. for four hours. Excess aqueous hydrochloric acid (3 N, 170 ml) is added and the solution concentrated under reduced pressure to give β-(4-methoxyphenyl)-5-oxo-2-pyrrolidinepropanoic acid and 3-(4-methoxyphenyl)-5-oxo-2-pyrrolidine-propanoic acid. The acids are dissolved in 300 ml of acetic anhydride, and the solution is heated to 90° C. The solution is filtered hot and the filtrate concentrated in vacuo. The oil is dissolved in chloroform, treated with activated carbon, filtered and concentrated. The oil is chromatographed on silica gel (200–400 mesh) (elution with chloroform) to give cis-and trans-dihydro-1-(4-methoxyphenyl)-1H-pyrrolizine-3,5(2H,6H)-dione as a white solid with a mp 125°–127° C.

NMR (CDCl$_3$) δ=6.90 (m, 4H); 4.62 (dt, J$_1$=6 Hz, J$_2$=9 Hz, ½H); 4.23 (dt, J$_1$=9 Hz, J$_2$=6 Hz, ½H); 3.73 (s, 3H) 3.61–1.57 (m, 7H).

IR (cm$^{-1}$) 2835, 1781, 1697, 1613, 1583, 1516, 1380, 1363, 1318.

I claim:

1. A compound having the structural formula:

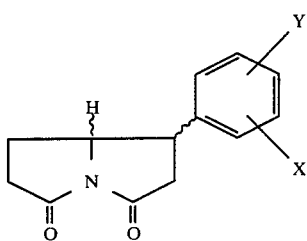

wherein X and Y are independently hydrogen, alkyl of from one to six carbon atoms, alkoxy of from one to six carbon atoms, chloro- or trifluoromethyl.

2. A compound in accordance with claim 1 wherein X and Y are independently hydrogen or alkyl of from one to six carbon atoms.

3. A compound in accordance with claim 1 wherein X and Y are independently hydrogen or alkoxy of from one to six carbon atoms.

4. A compound in accordance with claim 1 and being cis-dihydro-1-phenyl-1H-pyrrolizine-3,5[2H,6H]-dione.

5. A compound in accordance with claim 1 and being trans-dihydro-1-phenyl-1H-pyrrolizine-3,5[2H,6H]-dione.

6. A compound in accordance with claim 1 and being cis-dihydro-1-(4-methylphenyl)-1H-pyrrolizine-3,5-[2H,6H]-dione.

7. A compound in accordance with claim 1 and being trans-dihydro-1-(4-methylphenyl)-1H-pyrrolizine-3,5[2H,6H]-dione.

8. A compound in accordance with claim 1 and being cis-dihydro-1-(4-chlorophenyl)-1H-pyrrolizine-3,5[2H,6H]-dione.

9. A compound in accordance with claim 1 and being trans-dihydro-1-(4-chlorophenyl)-1H-pyrrolizine-3,5[2H,6H]-dione.

10. A compound in accordance with claim 1 and being cis-dihydro-1-(3,4-dichlorophenyl)-1H-pyrrolizine-3,5[2H,6H]-dione.

11. A compound in accordance with claim 1 and being trans-dihydro-1-(3,4-dichlorophenyl)-1H-pyrrolizine-3,5[2H,6H]-dione.

12. A compound in accordance with claim 1 and being cis-dihydro-1-(4-trifluoromethylphenyl)-1H-pyrrolizine-3,5[2H, 6H]-dione.

13. A compound in accordance with claim 1 and being trans-dihydro-1-(4-trifluoromethylphenyl)-1H-pyrrolizine-3,5[2H, 6H]-dione.

14. A compound in accordance with claim 1 and being cis-dihydro-1-(4-methyoxyphenyl)-1H-pyrrolizine-3,5[2H, 6H]-dione.

15. A compound in accordance with claim 1 and being trans-dihydro-1-(4-methoxyphenyl)-1H-pyrrolizine-3,5[2H, 6H]-dione.

16. A pharmaceutical composition for reversing electroconvulsive shock induced amnesia including an effective amount of a compound in accordance with claim 1 in combination with a pharmaceutically acceptable carrier.

17. A method of reversing electroconvulsive shock induced amnesia in a mammal comprising administering to said mammal in need of such treatment an effective amount of a pharmaceutical composition in accordance with claim 16.

* * * * *